US006830916B2

(12) United States Patent
Spiegel

(10) Patent No.: US 6,830,916 B2
(45) Date of Patent: Dec. 14, 2004

(54) SPHINGOSINE KINASE, CLONING, EXPRESSION AND METHODS OF USE

(76) Inventor: Sarah Spiegel, 6343 Linway Ter., McLean, VA (US) 22101

( * ) Notice: Subject to any disclaimer, the term of this patent is extended or adjusted under 35 U.S.C. 154(b) by 0 days.

(21) Appl. No.: 09/796,487

(22) Filed: Mar. 2, 2001

(65) Prior Publication Data
US 2002/0042358 A1 Apr. 11, 2002

Related U.S. Application Data

(63) Continuation-in-part of application No. 09/530,868, filed on May 5, 2000.
(60) Provisional application No. 60/186,352, filed on Mar. 2, 2000.

(51) Int. Cl.[7] ............................ C12N 9/48; C12N 1/20; C12N 15/00; C07H 21/04
(52) U.S. Cl. ................. 435/212; 435/252.3; 435/320.1; 536/23.2
(58) Field of Search .............................. 435/212, 252.3, 435/320.1, 194, 440; 536/23.2

(56) References Cited
PUBLICATIONS

Kohama et al. Molecular cloning and functional characterization of murine sphingosine kinase. The J. Biol. Chem. vol., 279, No. 37, pp. 23722–23728, 1998.*
Accession #AI972156. EST database. 1999.*

* cited by examiner

Primary Examiner—P. Achutamurthy
Assistant Examiner—Yong D. Pak
(74) Attorney, Agent, or Firm—Whitham, Curtis & Christofferson, P.C.

(57) ABSTRACT

The invention provides molecules that encode sphingosine kinase, the enzyme that catalyzes the phosphorylation of sphingosine to form sphingosine-1-phosphate (SPP). Vectors and host cells which express sphingosine kinase are also provided, as are methods for evaluating the stimulatory or inhibitory effects of agents on sphingosine kinase production and activity.

4 Claims, 3 Drawing Sheets

```
                                                                        123
              ↓         Pep-1           Pep-3    Pep-7                  ↘
SPHK1a    -------MEPECPRGLLPRPCRVLVLLNPQGGKGKALQLFQSRVQPFLEEAEITFKLILT    53
SPHK1b    MWWCCVLFVVECPRGLLPRPCRVLVLLNPQGGKGKALQLFQSRVQPFLEEAEITFKLILT
                                                                *     * 60

113
SPHK1a    ERKNHARELVCAEELGHWDALAVMSGDGLMHEVVNGLMERPDWETAIQKPLCSLPGGSGN
SPHK1b    ERKNHARELVCAEELGHWDALAVMSGDGLMHEVVNGLMERPDWETAIQKPLCSLPGGSGN
                                                                        120

173
SPHK1a    ALAASVNHYAGYEQVTNEDLLINCTLLLCRRRLSPMNLLSLHTASGLRLYSVLSLSWGFV
SPHK1b    ALAASVNHYAGYEQVTNEDLLINCTLLLCRRRLSPMNLLSLHTASGLRLYSVLSLSWGFV
                                  ◊                                     180

Pep-5                  Pep-2               Pep-4          237
SPHK1a    ADVDLESEKYRRLGEIRFTVGTFFRLASLRIYQGQLAYLPVGTVASKRPASTLVQKGPVD
SPHK1a    ADVDLESEKYRRLGEIRFTVGTFFRLASLRIYQGQLAYLPVGTVASKRPASTLVQKGPVD
              *                       *                    *           240

---------293
SPHK1a    THLVPLEEPVPSHWTVVPEQDFVLVLVLLHTHLSSELFAAPMGRCEAGVMHLFYVRAGVS
SPHK1b    THLVPLEEPVPSHWTVVPEQDFVLVLVLLHTHLSSELFAAPMGRCEAGVMHLFYVRAGVS
                                                                        300

353
SPHK1a    RAALLRLFLAMQKGKHMELDCPYLVHVPVVAFRLEPRSQRGVFSVDGELMVCEAVQGQVH
SPHK1b    RAALLRLFLAMQKGKHMELDCPYLVHVPVVAFRLEPRSQRGVFSVDGELMVCEAVQGQVH
                                                *                       360

Pep-6
SPHK1a    PNYLWMVCGSRDAPSGRDSRRGPPPEEP  381   504
SPHK1b    PNYLWMVCGSRDAPSGRDSRRGPPPEEP  388
              *      *
```

```
                                                              123
                                                               53
SPHK1a   --------MEPECPRGLLPRPCRVLVLLNPQGGKGKALQLFQSRVQPFLEEAEITFKLILT
SPHK1b   MWWCCVLFVVECPRGLLPRPCRVLVLLNPQGGKGKALQLFQSRVQPFLEEAEITFKLILT  60
                 Pep-1                  Pep-3   Pep-7           *
                                                              113
SPHK1a   ERKNHARELVCAEELGHWDALAVMSGDGLMHEVVNGLMERPDWETAIQKPLCSLPGGSGN
SPHK1b   ERKNHARELVCAEELGHWDALAVMSGDGLMHEVVNGLMERPDWETAIQKPLCSLPGGSGN  120
                                                                *
                                                              173
SPHK1a   ALAASVNHYAGYEQVTNEDLLINCTLLLCRRRLSPMNLLSLHTASGLRLYSVLSLSWGFV
SPHK1b   ALAASVNHYAGYEQVTNEDLLINCTLLLCRRRLSPMNLLSLHTASGLRLYSVLSLSWGFV  180
                                  ◇
                      Pep-5                 Pep-2             237
SPHK1a   ADVDLESEKYRRLGEIRFTVGTFFRLASLRIYQGQLAYLPVGTVASKRPASTLVQKGPVD
SPHK1b   ADVDLESEKYRRLGEIRFTVGTFFRLASLRIYQGQLAYLPVGTVASKRPASTLVQKGPVD  240
                                                    Pep-4       *
                                                              293
SPHK1a   THLVPLEEPVPSHWTVPEQDFVLVLVLLHTHLSSELFAAPMGRCEAGVMHLFYVRAGVS
SPHK1b   THLVPLEEPVPSHWTVPEQDFVLVLVLLHTHLSSELFAAPMGRCEAGVMHLFYVRAGVS   300
                                                                *
                                                              353
SPHK1a   RAALLRLFLAMQKGKHMELDCPYLVHVPVVAFRLEPRSQRGVFSVDGELMVCEAVQGQVH
SPHK1b   RAALLRLFLAMQKGKHMELDCPYLVHVPVVAFRLEPRSQRGVFSVDGELMVCEAVQGQVH  360
         Pep-6                                                  *
                         381   504
SPHK1a   PNYLWMVCGSRDAPSGRDSRRGPPPEEP
SPHK1b   PNYLWMVCGSRDAPSGRDSRRGPPPEEP  388
                  *
```

*Figure 1*

```
                    82    82  132       C1
Mouse SPHK1a    67        LLPRPCR VLVLLNPQGGKGKALQLFQSRVQ FFLEEAEITFKLILTERKN HARELVC-AEE   95
C elegans      (81)       EQCR-GN LLVFINPNSGTGKSLETFANTVGPK LDKSLIRYEVVVTGPN HARNVLMTKAD  140
Yeast LCB4     222        NSKRNRSI LVIINPHGGKGTAKNLFLIKARPI LVESGCKIEIAYTKYARH AIDIAK-DLD   280
Yeast LCB5     264        NTRRNKSI FVIINPFGGKGKAKKLFMTKAKPLL ASRCSIEVVYTKYPGH AIEIAR-EMD   322
Putavive Human            ........LNPRGGKGKALQLFRSH VQLLAEAEISFTLMLTERRN HARELVR-SEE Consenus                  .......R.....V.INP.GGKGKA..LF.....P.L........T....HA........D C3
Mouse SPHK1a    96        LGH WDALAVMSGDGLMHEVNGLMERPD WETAI -QKPLCS LPGGSGNALAAS VNHYAGYE   154
C elegans      141        LGK FNGVLILSGDGLVFEALNGILCREDA FRI FPTLPIGI VPSGSGNGLLCS VLSKYGTK   200
Yeast LCB4     281        ISK YDTIACASGDGIPYEVINGLYRRPDR VDA FNKLAVTQ LPCGSGNAMSIS CHWTNNPS    340
Yeast LCB5     323        IDK YDTIACASGDGIPHEVINGLYQRPDH VKA FNNIAITEI PCGSGNAMSVS CHWTNNPS    382
Putavive Human            LGR WDALVVMSGDGLMHEVNGLMERPD WETAI -QKPLCS LPAGSGNALAAS INHYAGYE Consenus                  .....D.LA..SGDGL..EVINGL.R.D...A.........P.GSGNA....S........

C4                                               C5
Mouse SPHK1a   220        LYS VLSLSWGF VADVDLESEKYRR-LGEIRFTVGTFR RLASLRIYQGLAYLPVGTVASK   278
C elegans      236        YAS FLSIGWGL MADIDIDSEKWRKSKGHHRFTVMGF IRSCNLRSYKGRLTYRPYKPKGFH   295
Yeast LCB4     370        RLS FLSQTYGV IAESDINTEFIRW-MGPVRFNLGVAF NIIQGKKYPCEVFVKYAAKSKKE   428
Yeast LCB5     412        KLS FLSQTYGL IAETDINTEFIRW-MGPARFELGVAF NIIQKKYPCEIYVKYAAKSKNE   470
Putavive Human            LRS VLSLAWGF IADVDLESEKYRR-LGEMRFTLGTFI RLAALRTYGRLATLPVGTVGSK Consenus                  ..S.LS.....G..A...DI.SE...R....G..RF...G.F.......R...........

504
Mouse SPHK1a   380        VVAFRLEPRSQRGVFSVDGELMVCEAVQGQVHPNYLWMVCGSRDAPSGRDSRRGPPPEEP  (439)
C elegans      431        VVSMKLEVISEGSHVVLDGEVVDTKTIEVASTKNHISVFSSTA--------------     473
Yeast LCB4     572        ILAYKIIPKVESGLFSVDGEKFPLEPLQVEIMPMLCKTLLRNGRYIDTEFESM-----    624
Yeast LCB5     635        ILAYKIIPKLGNGLFSVDGEKFPLEPLQVEIMPRLCKTLLRNGRYVDTDFDSM----     687
Putavive Human            VVAFRLEPRNGKGVEAVDGELMVSEAVQGQLHPNYLWM.....................

Consenus                  .....................F.VDGE...............................
```

*Figure 2*

```
                         *****
hSPHK1    1  MEPAGG PRGVLPRPCRVLVLLNPRGGKKALQLYMSRVQPL L AEAEITFY LILTERKNHA
mSPHK1a      MEPEC- PRGLLPRPCRVLVLLNPQGGKKALQLFQSRVQPF LEEAEITFK LILTERKNHA
                    ────────────────C1──────────────── hSPHK1   61  RELV REEELGHWDAL VMSGDGLMHEVVNGLMERPDWETAIQKPLCSLP AGSGNALAASL
mSPHK1a      RELV CAEELGHWDAL AVMSGDGLMHEVVNGLMERPDWETAIQKPLCSLP GGSGNALAASV
                 ─────────────────────C2─────────────────────        ──C3 hSPHK1  121  NHYAGYEQVTNEDLL TNCTLLLCRR LLSPMNLLSLHTASGLRLYSVLSLAWGFVADVDLE
mSPHK1a      NHYAGYEQVTNEDLL INCTLLLCRR RLSPMNLLSLHTASGLRLYSVLSLSWGFVADVDLE
                                       ──────────────C3────────────── hSPHK1  181  SEKYRRLGEMRFTLGTF LRLAALRT YRGKLAYLPVG RVGSKT PASPV VVQQGPVDAHLVP
mSPHK1a      SEKYRRLGEIRFTVGTE FRLASLRI YQGQLAYLPVG TVASKRPAS- TLVQKGPVDTHLVP
                                          ────────────C4──────────── hSPHK1  241  LEEPVPSHWTMVPDEDFVLILA LLHSHLG SEMFAAPMGRC AAGVMHLFYVRAGVSRA MLL
mSPHK1a      LEEPVPSHWTVVPEQDFVLVL VLLHTHLS SELFAAPMGRC EAGVMHLFYVRAGVSRA ALL
                                                       ────C5──── hSPHK1  301  R FFLAMEKGKHME YECPYLV VPVVAFRLEPRDG RGVFAVDGELMVCEAVQGQVHPNY FW
mSPHK1a      R LFLAMQKGKHME LDCPYLV HVPVVAFRLEPRS QRGVFSVDGELMVCEAVQGQVHPNY LW 384
hSPHK1  361  MVSGCVE PE FSVKPQ QMPP PEEP
mSPHK1a      MVCGSR DAP SGRDSR RGPP PEEP
```

Figure 3

SPHINGOSINE KINASE, CLONING, EXPRESSION AND METHODS OF USE

This application takes priority from Provisional Patent Application No. 60/186,352, which was filed Mar. 2, 2000 and is also a continuation-in-part of U.S. Ser. No. 09/530,868, which was filed on May 5, 2000 and was filed under rule 371 as the U.S. application from PCT/US99/11521.

FIELD OF THE INVENTION

This invention relates to sphingosine kinase, which catalyzes phosphorylation of sphingosine to form sphingosine-1-phosphate (SPP) and to molecules encoding sphingosine kinase, including mutants, variants, fragments and derivatives thereof, to vectors and transfected host cells which express sphingosine kinase. The present invention also relates to methods for evaluating stimulatory or inhibitory effects of agents on the sphingosine kinase production and activity.

BACKGROUND OF THE INVENTION

Sphingosine-1-phosphate (SPP), a sphingolipid metabolite, which regulates diverse biological processes, such as cell growth, differentiation, survival, motility, and calcium mobilization, is now emerging as a new member of a class of lipid signaling molecules with dual intra and intercellular actions. This phosphorylated derivative of sphingosine, the structural backbone of all sphingolipids, has many of the hallmarks of classical second messengers. The level of SPP is very low in cells and is rapidly increased by activation of sphingosine kinase (SPHK), the enzyme responsible for the formation of SPP. SPHK is a member of a highly conserved gene family and is distinct from other known lipid kinases. Changes in SPHK activity is induced by diverse physiological stimuli, including platelet-derived growth factor (PDGF), nerve growth factor (NGF), muscarinic acetylcholine agonists; TNF-a, activation of protein kinase C (PKC), and cross-linking of the immunoglobulin receptors. Like to other signaling molecules, SPP has a short half life due to rapid turnover catalyzed by SPP lyase and/or SPP phosphatase. Inhibition of SPP formation by competitive inhibitors of SPHK blunted the mitogenic response to PDGF, the cytoprotective effects of NGF, vitamin D3, PKC, and cAMP activators. Furthermore, calcium mobilization induced by FceR1, FcgR1, and muscarinic acetylcholine receptors are affected by SPP formation.

Because sphingosine-1-phosphate (SPP), acts both intracellularly and extracellularly to affect many biological processes, including mitogenesis, apoptosis, atherosclerosis and inflammatory responses, it is necessary to develop means of stimulating or inhibiting formation of SPP. Specific members of the EDG-1 family of G protein-coupled receptors bind SPP and modulate chemotaxis, angiogenesis neurite reaction and cell rounding. Because SPP levels are mainly regulated by the activity of SPHK, cloning and characterization of this enzyme are important for identifying normal and pathological processes. Hence, availability of the product of the invention as a means of evaluating effect on SPHK and SPP levels and activity is important for use in identifying agents that would inhibit or stimulate SPHK activity.

SUMMARY OF THE INVENTION

The SPHK has been purified from rat kidneys and subsequently identified in mouse cDNAs encoding two forms of SPHK, designated mSPHK1a and mSPHK1b, whose predicted proteins differ by only 10 amino acids at their N-terminus. Furthermore, the human SPHK cDNA (hSPHK) has now been defined. The corresponding mRNAs may arise by alternative splicing.

It is the purpose of this invention to provide SPHK, including human SPHK, and antibodies thereto for use in research, for use in diagnosis and for use in identifying agents which will inhibit or enhance activity of SPHK. The SPHK (using comparative control samples) and antibodies thereto may be used in diagnostic kits measuring the level of SPHK. SPHK activity is implicated as a contributing factor in several disease conditions, including cancer, stroke, atherosclerosis, inflammatory responses, allergic responses (including asthma) and Alzheimer's. The discovery of this invention makes it possible to test effect of drug candidates on inhibition and stimulation of activity of SPHK. Cell-free SPHK in a biologically non-toxic carrier can be added to substrates to evaluate drug candidates' effect on activity of hSPHK. It would, therefore, be possible to evaluate and propose dosages for drugs might either inhibit or stimulate SPHK activity.

DESCRIPTION OF THE FIGURES

FIG. 1 shows predicted amino acid sequences of two murine sphingosine kinases (SEQ ID NO:1 and SEQ ID NO:2).

FIG. 2 shows predicted amino acid sequence of hSPHK1 and alignment of the conserved domains. Mouse SPHK1a, amino acid residues 131 to 504 of mouse SPHK1a (SEQ ID NO: 5); C. elegans, amino acid sequence of C. elegans SPHK (SEQ ID NO: 6); Yeast LCB4, amino acid sequence of SPHK from the yeast LCB4 (SEQ ID NO: 7); Yeast LCB5, amino acid sequence of SPHK from the yeast LCB5 (SEQ ID NO: 8); Putative human, putative amino acid sequence of human SPHK (SEQ ID NO: 9).

FIG. 3 shows the domain structure of sphingosine kinase. hSPHK1, residues 1 to 384 of human SPHK-1 (SEQ ID NO: 3); mSPHK1a, amino acid residues 124 to 504 of mouse hSPHK1a (SEQ ID NO: 4).

DETAILED DESCRIPTION OF THE INVENTION

SPHK1 is ubiquitously expressed in adult tissues with highest levels in liver, kidney, lung and skeletal muscle. SPHK1 belongs to a family of highly conserved enzymes which differ from other known lipid kinases. It was the purpose of this invention to provide sphingosine kinases, including human sphingosine kinase, for use in identifying sphingosine kinase-inhibiting and stimulating agents, for laboratory research, and for evaluation of levels of sphingosine kinase in the clinical setting. The hSPHK may also be used for preparation of antibodies to sphingosine kinase in the human.

It is s purpose of this invention to provide means for inhibiting motility and chemotaxis of cells by enhancing intracellular formation of SPP. It is, furthermore, a purpose of the invention to provide sphingosine kinase and antibodies thereto for purposes research and for use in diagnostics.

The DNA fragment of about 1.9 kb encoding murine sphingosine kinase SPHK1a (381 amino acids) and SPHK1b (388 amino acids) deposited in GenBank at accession number AF068748 for SPHK1a and accession number Af068749 for SPHK1b. The human fragment has been

The present invention to provides a method for producing sphingosine kinase which comprises culturing a host cell under conditions such that the above-described DNA fragment is expressed and sphingosine kinase is thereby produced, and isolating sphingosine kinase for use as a reagent, for example for screening of drugs and inhibitors of sphingosine kinase and preparation of sphingosine-1-phosphate, for diagnosis, and for therapy.

The present invention to provide a method for detecting sphingosine kinase in a sample comprising:

(i) contacting a sample with antibodies which recognize sphingosine kinase; and (ii) detecting the presence or absence of a complex formed between sphingosine kinase and antibodies specific therefor.

Diagnostic kits may be made using antibodies raised to the SPHK. For example, the antibodies may be bound to microtiter plates or other supports for use in identifying SPHK at varying dilutions.

Because of the effect of SPP on rate of cell death and proliferation, it is possible, by inhibiting or stimulating the activity of SPHK. To increase healing, SPHK-stimulating agents may be used to enhance cell proliferation.

The use of antibodies to SPHK or inhibitors of SPHK activity can be used to ameliorate diseases caused by excess proliferation of cells.

Materials and Methods:

Sphingosine-1-phosphate (SPP), N,N-dimethylsphingosine (DMS) and sphingosine were obtained from Biomol Research Laboratory Inc. (Plymouth Meeting, Pa.). All other lipids were purchased from Avanti Polar Lipids (Birmingham, Ala.). ($\tau$-$^{32}$P]ATP (300 Ci/mmol) was purchased from Amersham (Arlington Heights, Ill.). Poly L-lysine was from Boehringer Mannheim (Indianapolis, Ind.). Alkaline phosphatase was from bovine intestinal mucosa, Type VII-NT, was from Sigma (St. Louis, Mo.). Restriction enzymes were from New England Biolabs (Beverly, Mass.) Lipofectamine PLUS and Lipofectamine were from Life Technologies, Inc. (Gaithersburg, Md.). Monoclonal antibodies against c-myc were from Zymed (San Francisco, Calif.), and anti-mouse Texas Red dye-conjugated goat antibody was from Jackson Immunoresearch (West Grove, Pa.). The Anti-Fade kit was from Molecular Probes (Eugene, Oreg.). The bromodeoxyuridine incorporation detection kit and anti-mouse FITC-conjugated IgG were obtained from Boehringer Mannheim (Indianapolis, Ind.). Bisbenzimide hydrochloride (Hoechst #33258) was from Calbiochem (San Diego. Calif.). Silica Gel 60 G plates were from EM Sciences (Cherry Hill, N.J.). Mouse 2.5S nerve growth factor was obtained from Upstate Biotechnology Inc. (Lake Placid, N.Y.). Sprague Dawley rat tissues were from Pelfreeze (Rogers, Ariz.).

Protein Sequencing of Sphingosine Kinase:

Purified sphingosine kinase was electrophoresed on SDS-PAGE and the Coomassiestained 49 kd band excised. After S-carboxy-amidomethylation, this band was subjected to in-gel tryptic digestion as described. The resulting peptide mixture was separated by microbore high performance liquid chromatography on a Zorbax C18 1.0 mm by 150-mm reverse-phase column in a Hewlett-Packard 1090 HPLC with a 1040 diode array detector. Fractions were selected for sequencing based on differential UV absorbance at 205, 277, and 292 nm, and the peptide sequences were determined by automated Edman degradation. Complementary peptide sequence information was also obtained on 10% of the digest mixture by collisionally induced dissociation using microcapillary HPLC electrospray ionization/tandem mass spectrometry on a Finnigan TSQ7000 triple quadruple mass spectrometer. Sequences of smaller peaks were determined on an Applied Biosystems Procise cLC 494 sequencer or by microcapillary HPLC-MS as above or on a Finnigan Laser-Mat 2000 Time-of-Flight Mass Spectrometer Matrix-assisted Laser Desorption TOF/MS (MALDI-TOFMS).

Sequencing and Cloning of Sphingosine Kinase:

The 49 kD sphingosine kinase polypeptide, purified from rat kidney, was excised from an SDS gel and subjected to trypsin digestion. The resulting peptides were separated by microcapillary reverse-phase HPLC and sequences of 8 peptides were determined by Edman degradation or MALDI mass spectrometry.

Homology searches (BLAST) against a comprehensive nonredundant database revealed no matches to known proteins. However, when the database of expressed sequence tags (dbEST) at NCBI was searched using the tBLASTn algorithm, an EST (Genbank accession number AA011725) containing sequences homologous to 3 of the 8 peptides (peptides 5, 2, and 4) was retrieved. A further search with peptides 1, 3 and 7 yielded 4 additional ESTs (Genbank accession numbers AA000819, AA107451, AA592274, and AA389543). The nucleotide sequences of mouse ESTs AA000819 and AA592274 were then used to search dbEST to obtain EST AA389187. Clones AA107451 and AA389187 were highly homologous at their 3 ends, but were slightly divergent at their 5' ends. sequencing of the full-length cDNAs revealed apparent open reading frames coding for 381 and 388 amino acid polypeptides containing sequences highly homologous to seven isolated peptides distributed throughout the protein, and these are thus designated SPHK1a and SPHK1b. In addition, both contained a portion of peptide 8. SPHK1a and 1b have predicted pIs of 6.68 and 6.89 and MWs of 42344 and 43254, respectively, in agreement with the MW of purified rat kidney sphingosine kinase. Because SPHK1b only differs by a few amino acids at the N terminus, it may arise by alternative splicing. However, both sequences lacked Kozak concensus sequences, suggesting that these cDNAs may not include the actual initiation sequences.

SPHK1a has 2 overlapping calcium/calmodulin binding consensus sequences of the 1-8-14 Type B motif ((FILVW) xxxxxx(FAILVW)xxxxx(FILVW), containing net positive charges of 2–4). In addition, near the C-terminus, SPHK1a contains 2 overlapping calcium/calmodulin binding consensus sequences, one of Type B and one of Type A ((FILVW) xxx(FAILVW)xx(FAILVW)xxxxx(FILVW)) containing net positive charges of 3–6). SPHK1b contains all the above calcium/calmodulin binding consensus sequences as well as an additional Type B motif at the N-terminus. The existence of multiple calcium/calmodulin binding motifs supports previous observations that purified rat kidney sphingosine kinase binds tightly to calmodulin-sepharose in the presence of calcium.

Analysis of the domain structure of SPHK1a obtained by searching the protein data base (GenBank and Prosite) revealed several putative post-translational phosphorylation motifs: one kinase A, two casein kinase II, and eight protein kinase C phosphorylation sites. Interestingly, it was previously demonstrated that inhibition of ceramide-induced apoptosis by protein kinase C activation results from stimulation of sphingosine kinase and concomitant increase in cellular SPP levels. Sphingosine kinase is thought to be mainly a cytosolic enzyme. Consistent with this, a hydropathy plot indicates that SPHK1a does not contain signal peptide or hydrophobic transmembrane sequences (data not shown).

Human Sphingosine Kinase cDNA Cloning:

BLAST searches using mSPHK1a sequences identified an EST clone (AA026479) which contained sequences homologous to several conserved domains of mSPHK. Human sphingosine kinase 1 was cloned by RT-CPR using poly(A)+ RNA from HEK293 cells and a gene-specific antisense primer hspk1-ASP1:5'-ACCATTGTCCAGTGAG The cDNA was extended by 5'RACE (Life Technologies) with two consecutive PCR (polymerase chain reaction) reactions using LA Taq (TaKaRa). First PCTR:5'RACE (rapid amplification of cDNA ends) Abridged Anchor Primer and the antisense primer hspk1-GSP2, 5'-TTCCTACAGGGAGGTAGGCC at 94° C. for 2 minutes followed by 30 cycles of amplification (94° C. for 1 minute, 55° C. for 1 minute, 72° C. for 2 minutes) and primer extension at 72° C. for 5 minutes. Second PCR:Abridged Universal Amplification Primer and the antisense primer hspk1-GSP 3,5'-GGCTGCCAGACGCAGGAAGG using a program similar to the first PCR but with annealing at 65° C. The PCR products were cloned into pCR2.1 (TA cloning, Invitrogen) and sequences confirmed by automated sequencing. To make expression constructs, a primer set was designated as follows: sense primer containing Kozak sequence and ATG start codon, sphk1-GSP4 (5'-GCCACCATGGATCCAGCGGGCGGCCCC); antisense primer, sphk1-GSP5 (5'TCATAAGGGCTCTTCTGGCGGTGGCATCTG). The PCR reaction was performed using human fetus Marathon-Ready cDNA (Clontech) as template with the above primers, and the amplification product was subcloned into pCR3.1 (Eukaryotic TA Cloning, Invitrogen). In addition, hSPHK1 was tagged at the N-terminus by subcloning into a pcDNA-c-myc vector using high fidelity taq polymerase (Pfu, Stratagene). hSPHK1 accession number is AF238083.

Cell Culture and Expression of Sphingosine Kinase:

Human embryonic kidney cells (HEK293, ATCC CRL-1573) were grown in high glucose Dulbecco's modified Eagle's medium (DMEM) containing 100 U/ml penicillin, 100 µg/ml streptomycin and 2 mM L-glutamine supplemented with 10% fetal bovine serum. Cells were transfected with either pcDNA3.1 or pCR3.1 containing hSPHK1 using Lipofectamine Plus according to the manufacturer's protocol. Transfection efficiencies were typically about 40%.

Measurement of Sphingosine Kinase Activity:

Cytosolic sphingosine kinase activity was determined with 50 µM sphingosine dissolved in Triton X-100 (final concentration 0.25%) and [τ-$^{32}$]ATP (10 µCi, 1 mM) containing MgCl$_2$ (10 mM). In some studies, sphingosine was added as a complex with bovine serum albumin (BSA). Specific activity was expressed as pmol SPP formed per minute per mg protein.

Lipid Extraction and Measurement of SPP, Sphingosine and Ceramide:

Cells were washed with PBS and scraped in 1 ml of methanol containing 2.5 µl concentrated HCl. Lipids were extracted by adding 2 ml chloroform/1M NaCl (1:1, v/v) and 100 µl 3N NaOH. The phases were separated. The basic aqueous phase containing SPP and devoid of sphingosine, ceramide and the majority of phospholipids was transferred to a siliconized glass tube. The organic phases were re-extracted with 1 ml methanol/1 M NaCl (1:11, v;/v) plus 50 µl 3N NaOH, and the aqueous factions were the combined. mass measurements of SPP in the aqueous phase were carried out as previously described. Sphingosine and ceramide in the organic phase were determined by enzymatic methods using sphingosine kinase and diacylglycerol kinase, respectively. Total phospholipids present in lipid extracts was also quantified.

Northern Blotting Analysis:

Poly(A)+ RNA blots containing 2 µg of poly(A)+ RNA per lane from multiple adult human tissues (Clontech) were hybridized with the 0.6 kb EcoRV/Sphl fragment of pCR3.1-hSPHK1, which was gel-purified and labeled with [$^{32}$P] dCTP by random priming. Hybridization in ExpressHyb buffer (Clontech) was carried out a 65° C. overnight according to the manufacturer's protocol. Blots were reprobed with a human β-actin control probe (Clontech). Bands were quantified using a Molecular Dynamics Phosphoimager.

Cloning of hSPHK1:

BLAST searches of the est database identified a human homologue of murine SPHK, EST AA026479, with similarity to the 3' end of mSPHK1a. This sequence was used to design specific primers and 5'RACE was performed on mRNA extracted from HEK293 cells to obtain the full-length cDNA of hSPHK1. The open reading frame encodes a protein with 384 amino acids having 85% identity and 92% similarity to mSPHK1a at the amino acid level. The figure indicates that Clustra/W alignment of SPHKs from mouse and human show the identical and conserved amino acid substitutions shaded dark and light gray, respectively. The conserved domains (C1 to C5) are indicted by lines and the invariant positively charged motif, GGKGK by asterisks. By sequence alignment it was previously found that SPHKs from mouse, yeast and C. elegans share several conserved blocks of amino acids. Similarly, hSPHK1 contains conserved regions, including the invariant positively charged motif, GGKGK, in the C1 domain, which may be part of the ATP binding site of this class of lipid kinases.

Recombinant Sphingosine Kinase Activity:

To investigate whether SPHK1a and SPHK1b encode bona fide sphingosine kinases, HEK293 cells were transiently transfected with pCMVSPORT2 expression vectors containing either SPHK1a or SPHK1b cDNAs and sphingosine kinase activity was measured. Modest levels of endogenous sphingosine kinase activity were present in control cells (either untransfected or transfected with an empty vector). Cells transfected with SPHK1a exhibited 300-fold increased sphingosine kinase activity 24 h after transfection that remained at this level for 4 days. In contrast, cells transfected with SPHK1b showed only 120 fold increased sphingosine kinase activity after 24 h and then decreased gradually to control levels after 4 days. Transfection of either Swiss 3T3 or NIH 3T3 fibroblasts with SPHK1a or SPHK1b also resulted in marked increases in sphingosine kinase activity. As in HEK293 cells, transfection of 3T3 cells with SPHK1a led to much larger increases in sphingosine kinase activity than with SPHK1b. It should be noted that transfection efficiency was quite good and similar in all three cell lines.

hSPHK1 Encodes a Functional Sphingosine Kinase:

HEK293 cells were transfected with expression vectors containing hSPHK1 to determine whether it encodes a bonafide SPHK. HEK293 cells were transiently transfected with empty vector or vector containing either mSPHK1a or hSPHK1. SPHK activity was measured in cytosol and particulate pellet 24 hours after transfection using sphingosine-BSA complexes or sphingosine-Triton X-100 micelles as substrate as indicated. SPHK activity in vector-transfected cells was 84±2 and 134±27 pmol/min/mg using sphingosine-BSA complexes or sphingosine-Triton X-100 micelles as substrate, respectively. Data are means ±SD and are representative of two independent tests. In other words, modest levels of endogenous SPHK activity were detected in cells transfected with an empty vector. Twenty four hours after transfection with pcDNA3.1, 2-hSPHK1, the SPHK activity increased approximately 600 fold and remained at this level for at least 2 days. For comparison, a similar increase in activity was observed after transfection with mSPHK1a. Similar results were obtained when cells were transfected with hSPHK1 in pCR3.1. In agreement with previous results with mSPHK1a, hSPHK1 was stimulated by Trition X-100. In cells transfected with hSPHK1, approximately 70% of the SPHK activity was found in the cytosol and only about 30% was membrane-associated. Kyte-Doolittle hydropathy plots did not suggest the presence of any potential hydrophobic membrane spanning domains in the primary structure of hSPHK1.

Transfection of HEK293 cells with hSPHK1 also resulted in changes in levels of sphingolipid metabolites. Mass levels of SPP, sphingosine and increased 5.7 fold compared to cells transfected with vector alone, with an 18% decrease in levels of both sphingosine and ceramide. However, because intracellular ceramide pools are much larger than sphingosine pools, the absolute decrease of ceramide was greater than the decrease in sphingosine mass. Hence, it is seen that hSPHK1 appeared active in intact cells and that kinase overexpression can alter the intracellular balance of sphingolipid metabolites.

Substrate Specificity of hSPHK1:

When HEK293 cells were transiently transfected with empty vector or vector containing either mSPHK1a or hSPHK1. SPHK activity was measured in cytosol and particulate pellet 24 h after transfection using sphingosine-BSA complexes or sphingosine-Triton X-100 micelles as substrate as indicated. SPHK activity in vector transfected cells was 84±2 and 134±27 pmol/min/mg using sphingosine-BSA complexes or sphingosine-Triton X-100 micelles as substrate, respectively. Data are means±SD and are representative of two independent experiments. Changes in mass levels of SPP, sphingosine, and ceramide were noted. Mass levels of SPP, sphingosine and ceramide in cells transfected with empty vector or vector containing hSPHK1 were measured after 24 h. Data are expressed as pmol per nmol phospholipid and are means±SD.

HEK293 cells were transfected with hSPHK1 and SPHK-dependent phosphorylation of various sphingosine analogs or other lipids (50 µM) was measured using cell lysates as enzyme source. DAG, diacylglycerol; PI, phosphatidylinositol; C2-CER, N-acetyl—sphingosine. N,N-Dimethylsphingosine and D,L-threo-dihydro-sphingosine are inhibitors of hSPHK1. SPHK activity in HEK293 cell lysates 24 h after transfection with hSPHK1 was measured with 10 µM SPP in the absence or presence of 20 µM and 40 µM DMS or DHS. Data are means±SD and are expressed as percent inhibition.

The naturally occurring D-(+)-erythro-trans-isomer of sphingosine and erythrodihydrosphingosine (sphingamine) were the best substrates for hSPHK1. As with the SPHK1a, sphingosine was more efficiently phosphorylated than sphingamine. Moreover, the sphingolipids, including D,L-threo-dihydrosphingosine (DHS) and C2-ceramide, as well as diacylglycerol and phosphatidylinositol, were not substrates. With D-erythro-sphingosine as substrate, half-maximal velocity was found at 5 µM in excellent agreement with Km values previously determined with rat kidney SPHK and recombinant mSPHK1a. CMS and DHS have previously been used to inhibit SPHK and block increases in SPP induced by various physiological stimuli. Both of these sphingolipids also inhibited hSPHK1 and, as seen with inhibitory effects of mSPHK1a, DHS was slightly more potent thank DMS in this testing.

Tissue Distribution of hSPHK1 Expression:

The tissue distribution of SPHK1 MRNA expression in adult human tissues was analyzed by Northern blotting. In most tissues, including adult brain, heart, spleen, lung, kidney and testis, a predominant 1.9 kb mRNA species was detected. Expression was highest in adult liver, heart and skeletal muscle. In comparison, it was shown that mSPHK1a expression is greatest in mouse spleen, lung, kidney, testes and heart, with much lower expression in skeletal muscle.

Adhesion Assay:

Collagen I (0.1 mg/ml), fibronectin (0.5 mg/ml), polylysine (0.1 mg/ml), or Matrigel (1:10 dilution) were added into wells of a 6-well culture plate and incubated for 45–60 min at room temperature. Plates were then incubated with 3% BSA in PBS for 30 min to block non-specific binding sites followed by three washes with PBS. NIH 3T3 fibroblasts were harvested by scraping in PBS/10 mM EDTA, washed and resuspended in DMEM/BSA at $10^5$ cells/ml, and 2 ml suspensions were then added to each well and incubated at 37° C. for the indicated time. Non-adherent cells were removed and attached cells fixed with 70% ethanol for 20 min and stained with crystal violet. Wells were gently rinsed three times with water and allowed to dry. Incorporated dye was dissolved in 100 µl/well of 0.1 M sodium citrate in 50% ethanol (pH 4.2) and the absorbance measured at 540 nm.

SPHK activity in NIH 3T3 and HEK293 cells stably expressing c-myc tagged SPHK1a was dramatically increased by 500 fold. Western blot analysis of cytosolic fractions using anti-c-myc antibody revealed a specific protein band with an apparent molecular weight consistent with the predicted size of c-myc-SPHK which was absent in vector transfected cells. SPP levels were also elevated in cells expressing SPHK, although the increases were only 4–8 fold and did not correlate with the large fold increase in SPHK activity measured in vitro. One possible explanation for this discrepancy is that availability of cellular sphingosine might limit the production of SPP.

Since activated platelets can release SPP and a family of G protein-coupled SPP receptors have been identified, it was important to determine whether SPHK-transfected cells, which have notable increases in SPP levels, secrete SPP into the medium. No significant release of SPP into the extracellular media could be detected, even after addition of sphingosine. To increase the sensitivity of detection of secreted SPP, cells were labeled to isotopic equilibrium with [$^{32}$P]$p_i$ and analyzed the labeled SPP in cells as well as in the medium. Despite the large increases in [$^{32}$P]SPP detected in cells overexpressing SPHK, there was no detectable labeled SPP released into the medium. Both SPP assays gave identical increases in intracellular SPP in transfected and sphingosine-treated cells. Based on the sensitivity of these methods (1–2 pmol of SPP/sample), it is estimated that the concentration of SPP in the extracellular media must be less than 0.4 nM, a concentration well below the Ec50 for binding of SPP to its receptors.

Most of the SPHK activity in cells stably expressing c-myc-tagged SPHK was cytosolic (data not shown), suggesting that the small c-myc-tag does not affect localization of SPHK. Immunohistochemistry with antibodies against c-myc revealed that SPHK has a diffuse distribution in the cytosol and somewhat denser expression in perinuclear sites.

PDGF stimulated cytosolic c-myc-SPHK activity in transfected NIH 3T3 fibroblasts to a similar extent as its effect on endogenous SPHK, indicating that c-myc-SPHK activity is regulated by the signaling pathways triggered by growth factors in the same manner as the native enzyme. Collectively, these data show that cells overexpressing SPHK are a useful tool to study intracellular actions of SPP.

Previously, many studies have shown that exogenous SPP inhibits chemotactic and haptotactic motility of various cancer cells by binding to putative cell surface receptors. Furthermore, Yamamura et al. found that low nanomolar concentrations of SPP and SPP immobilized on controlled pore glass beads inhibited the motility of mouse melanoma B10 cells. Thus, it was expected that overexpression of SPHK, which increases endogenous, but not secreted SPP, should not affect cellular movement. Surprisingly, chemotaxis directed towards concentration gradients of PDGF and serum was markedly reduced in NIH 3T3 and HEK293 cells transiently or stably overexpressing SPHK. Although chemotaxis measurements were routinely performed over a 24 h period with a potent chemoattractant such as PDGF, the inhibitory effect of SPP was discernible as soon as 6 h.

Moreover, expression of SPHK also inhibited chemokinesis, or random cell motility, albeit to a lesser extent. To determine whether the effect of SPHK on motility was due to altered adhesion to the collagen I-coated filters used in the Boyden chamber assay, adherence to collagen I was determined. The time-course of adhesion to plastic or collagen I coated-wells was similar for vector and SPHK-transfected cells. Overexpression of SPHK had no significant effects on the adhesiveness of cells not only to collagen, but also to fibronectin, Matrigel, and poly-lysine. Thus, intracellular SPP, rather than secreted SPP, regulates chemotactic motility without affecting adhesion of cells to their substratum.

---

SEQUENCE LISTING

```
<160> NUMBER OF SEQ ID NOS: 17

<210> SEQ ID NO 1
<211> LENGTH: 381
<212> TYPE: PRT
<213> ORGANISM: Mus musculus
<220> FEATURE:
<221> NAME/KEY: MISC_FEATURE
<222> LOCATION: (1)..(381)
<223> OTHER INFORMATION: SEQ ID NO 1 is the peptide sequence of SPHK1a
      in Figure 1, corresponding to amino acid residue 124 to 504 of
      SPHK1a of GenBank sequence Accession Number AAC61697. SEQ ID NO 1
      is equivalent to SEQ ID NO 4 that is the amino acid sequence of
      mSPHK1a in Figure 3.
<300> PUBLICATION INFORMATION:
<301> AUTHORS: Kohama et al.
<302> TITLE: Molecular cloning and fuctional characterization of murine
      sphingosin kinase
<303> JOURNAL: Journal of Biological Chemistry
<304> VOLUME: 237
<305> ISSUE: 37
<306> PAGES: 23722-23782
<307> DATE: 1998
<308> DATABASE ACCESSION NUMBER: AAC61697
<309> DATABASE ENTRY DATE: 1998-09-26
<313> RELEVANT RESIDUES: (124)..(504)
<300> PUBLICATION INFORMATION:
<308> DATABASE ACCESSION NUMBER: AAC61697
<309> DATABASE ENTRY DATE: 1998-09-26
<313> RELEVANT RESIDUES: (124)..(504)

<400> SEQUENCE: 1

Met Glu Pro Glu Cys Pro Arg Gly Leu Leu Pro Arg Pro Cys Arg Val
1               5                   10                  15

Leu Val Leu Leu Asn Pro Gln Gly Gly Lys Gly Lys Ala Leu Gln Leu
            20                  25                  30

Phe Gln Ser Arg Val Gln Pro Phe Leu Glu Glu Ala Glu Ile Thr Phe
        35                  40                  45

Lys Leu Ile Leu Thr Glu Arg Lys Asn His Ala Arg Glu Leu Val Cys
    50                  55                  60

Ala Glu Glu Leu Gly His Trp Asp Ala Leu Ala Val Met Ser Gly Asp
65                  70                  75                  80

Gly Leu Met His Glu Val Val Asn Gly Leu Met Glu Arg Pro Asp Trp
                85                  90                  95

Glu Thr Ala Ile Gln Lys Pro Leu Cys Ser Leu Pro Gly Gly Ser Gly
            100                 105                 110

Asn Ala Leu Ala Ala Ser Val Asn His Tyr Ala Gly Tyr Glu Gln Val
        115                 120                 125

Thr Asn Glu Asp Leu Leu Ile Asn Cys Thr Leu Leu Leu Cys Arg Arg
    130                 135                 140
```

```
Arg Leu Ser Pro Met Asn Leu Ser Leu His Thr Ala Ser Gly Leu
145                 150                 155                 160

Arg Leu Tyr Ser Val Leu Ser Leu Ser Trp Gly Phe Val Ala Asp Val
            165                 170                 175

Asp Leu Glu Ser Glu Lys Tyr Arg Arg Leu Gly Glu Ile Arg Phe Thr
            180                 185                 190

Val Gly Thr Phe Phe Arg Leu Ala Ser Leu Arg Ile Tyr Gln Gly Gln
        195                 200                 205

Leu Ala Tyr Leu Pro Val Gly Thr Val Ala Ser Lys Arg Pro Ala Ser
        210                 215                 220

Thr Leu Val Gln Lys Gly Pro Val Asp Thr His Leu Val Pro Leu Glu
225                 230                 235                 240

Glu Pro Val Pro Ser His Trp Thr Val Val Pro Glu Gln Asp Phe Leu
                245                 250                 255

Leu Val Leu Val Leu Leu His Thr His Leu Ser Ser Glu Leu Phe Ala
                260                 265                 270

Ala Pro Met Gly Arg Cys Glu Ala Gly Val Met His Leu Phe Tyr Val
            275                 280                 285

Arg Ala Gly Val Ser Arg Ala Ala Leu Leu Arg Leu Phe Leu Ala Met
        290                 295                 300

Gln Lys Gly Lys His Met Glu Leu Asp Cys Pro Tyr Leu Val His Val
305                 310                 315                 320

Pro Val Val Ala Phe Arg Leu Glu Pro Arg Ser Gln Arg Gly Val Phe
                325                 330                 335

Ser Val Asp Gly Glu Leu Met Val Cys Glu Ala Val Gln Gly Gln Val
            340                 345                 350

His Pro Asn Tyr Leu Trp Met Val Cys Gly Ser Arg Asp Ala Pro Ser
        355                 360                 365

Gly Arg Asp Ser Arg Arg Gly Pro Pro Pro Glu Glu Pro
    370                 375                 380

<210> SEQ ID NO 2
<211> LENGTH: 388
<212> TYPE: PRT
<213> ORGANISM: Mus Musculus
<220> FEATURE:
<221> NAME/KEY: MISC_FEATURE
<222> LOCATION: (1)..(388)
<223> OTHER INFORMATION: SEQ ID NO 2 is the peptide sequence of SPHK1b
      in Fig. 1, corresponding to amino acid residue 1 to 388 of SPHK1b
      of GenBank sequence Accession Number AAC61698.
<300> PUBLICATION INFORMATION:
<301> AUTHORS: Kohama et al.
<302> TITLE: Molecular cloning and fuctional characteriation of murine
      sphingosine kinase
<303> JOURNAL: Journal of Biological Chemistry
<304> VOLUME: 273
<305> ISSUE: 37
<306> PAGES: 23722-23728
<307> DATE: 1998
<308> DATABASE ACCESSION NUMBER: AAC61698
<309> DATABASE ENTRY DATE: 1998-09-26
<313> RELEVANT RESIDUES: (1)..(388)
<300> PUBLICATION INFORMATION:
<308> DATABASE ACCESSION NUMBER: AAC61698
<309> DATABASE ENTRY DATE: 1998-09-26
<313> RELEVANT RESIDUES: (1)..(388)

<400> SEQUENCE: 2

Met Trp Trp Cys Cys Val Leu Phe Val Val Glu Cys Pro Arg Gly Leu
1               5                   10                  15
```

```
Leu Pro Arg Pro Cys Arg Val Leu Val Leu Asn Pro Gln Gly Gly
         20                  25                  30
Lys Gly Lys Ala Leu Gln Leu Phe Gln Ser Arg Val Gln Pro Phe Leu
         35                  40                  45
Glu Glu Ala Glu Ile Thr Phe Lys Leu Ile Leu Thr Glu Arg Lys Asn
 50                  55                  60
His Ala Arg Glu Leu Val Cys Ala Glu Glu Leu Gly His Trp Asp Ala
 65                  70                  75                  80
Leu Ala Val Met Ser Gly Asp Gly Leu Met His Glu Val Val Asn Gly
                 85                  90                  95
Leu Met Glu Arg Pro Asp Trp Glu Thr Ala Ile Gln Lys Pro Leu Cys
             100                 105                 110
Ser Leu Pro Gly Gly Ser Gly Asn Ala Leu Ala Ala Ser Val Asn His
             115                 120                 125
Tyr Ala Gly Tyr Glu Gln Val Thr Asn Glu Asp Leu Leu Ile Asn Cys
         130                 135                 140
Thr Leu Leu Leu Cys Arg Arg Arg Leu Ser Pro Met Asn Leu Leu Ser
145                 150                 155                 160
Leu His Thr Ala Ser Gly Leu Arg Leu Tyr Ser Val Leu Ser Leu Ser
                 165                 170                 175
Trp Gly Phe Val Ala Asp Val Asp Leu Glu Ser Glu Lys Tyr Arg Arg
             180                 185                 190
Leu Gly Glu Ile Arg Phe Thr Val Gly Thr Phe Phe Arg Leu Ala Ser
             195                 200                 205
Leu Arg Ile Tyr Gln Gly Gln Leu Ala Tyr Leu Pro Val Gly Thr Val
         210                 215                 220
Ala Ser Lys Arg Pro Ala Ser Thr Leu Val Gln Lys Gly Pro Val Asp
225                 230                 235                 240
Thr His Leu Val Pro Leu Glu Glu Pro Val Pro Ser His Trp Thr Val
                 245                 250                 255
Val Pro Glu Gln Asp Phe Val Leu Val Leu Val Leu His Thr His
             260                 265                 270
Leu Ser Ser Glu Leu Phe Ala Ala Pro Met Gly Arg Cys Glu Ala Gly
             275                 280                 285
Val Met His Leu Phe Tyr Val Arg Ala Gly Val Ser Arg Ala Ala Leu
         290                 295                 300
Leu Arg Leu Phe Leu Ala Met Gln Lys Gly Lys His Met Glu Leu Asp
305                 310                 315                 320
Cys Pro Tyr Leu Val His Val Pro Val Ala Phe Arg Leu Glu Pro
                 325                 330                 335
Arg Ser Gln Arg Gly Val Phe Ser Val Asp Gly Glu Leu Met Val Cys
             340                 345                 350
Glu Ala Val Gln Gly Gln Val His Pro Asn Tyr Leu Trp Met Val Cys
             355                 360                 365
Gly Ser Arg Asp Ala Pro Ser Gly Arg Asp Ser Arg Arg Gly Pro Pro
         370                 375                 380
Pro Glu Glu Pro
385

<210> SEQ ID NO 3
<211> LENGTH: 384
<212> TYPE: PRT
<213> ORGANISM: Homo sapiens
<220> FEATURE:
<221> NAME/KEY: MISC_FEATURE
```

```
<222> LOCATION: (1)..(384)
<223> OTHER INFORMATION: SEQ ID NO 3 is the peptide sequence of hSPHK1
      in Fig. 3, corresponding to amino acid residue 1 to 384 of Homo
      sapiens SPHK-1 of GenBank sequence Accession Number AAF73423.
<300> PUBLICATION INFORMATION:
<301> AUTHORS: Nava et al.
<302> TITLE: Functional characterization of human spingosine kinase-1
<303> JOURNAL: FEBS Lett.
<304> VOLUME: 473
<305> ISSUE: 1
<306> PAGES: 81-84
<307> DATE: 2000
<308> DATABASE ACCESSION NUMBER: AAF73423
<309> DATABASE ENTRY DATE: 2000-06-01
<313> RELEVANT RESIDUES: (1)..(384)
<300> PUBLICATION INFORMATION:
<308> DATABASE ACCESSION NUMBER: AFF73423
<309> DATABASE ENTRY DATE: 2000-06-01
<313> RELEVANT RESIDUES: (1)..(384)

<400> SEQUENCE: 3

Met Asp Pro Ala Gly Gly Pro Arg Gly Val Leu Pro Arg Pro Cys Arg
1               5                   10                  15

Val Leu Val Leu Leu Asn Pro Arg Gly Gly Lys Gly Lys Ala Leu Gln
            20                  25                  30

Leu Phe Arg Ser His Val Gln Pro Leu Leu Ala Glu Ala Glu Ile Ser
        35                  40                  45

Phe Thr Leu Met Leu Thr Glu Arg Arg Asn His Ala Arg Glu Leu Val
50                  55                  60

Arg Ser Glu Glu Leu Gly Arg Trp Asp Ala Leu Val Val Met Ser Gly
65                  70                  75                  80

Asp Gly Leu Met His Glu Val Val Asn Gly Leu Met Glu Arg Pro Asp
                85                  90                  95

Trp Glu Thr Ala Ile Gln Lys Pro Leu Cys Ser Leu Pro Ala Gly Ser
            100                 105                 110

Gly Asn Ala Leu Ala Ala Ser Leu Asn His Tyr Ala Gly Tyr Glu Gln
        115                 120                 125

Val Thr Asn Glu Asp Leu Leu Thr Asn Cys Thr Leu Leu Leu Cys Arg
130                 135                 140

Arg Leu Leu Ser Pro Met Asn Leu Leu Ser Leu His Thr Ala Ser Gly
145                 150                 155                 160

Leu Arg Leu Phe Ser Val Leu Ser Leu Ala Trp Gly Phe Ile Ala Asp
                165                 170                 175

Val Asp Leu Glu Ser Glu Lys Tyr Arg Arg Leu Gly Glu Met Arg Phe
            180                 185                 190

Thr Leu Gly Thr Phe Leu Arg Leu Ala Ala Leu Arg Thr Tyr Arg Gly
        195                 200                 205

Arg Leu Ala Tyr Leu Pro Val Gly Arg Val Gly Ser Lys Thr Pro Ala
210                 215                 220

Ser Pro Val Val Gln Gln Gly Pro Val Asp Ala His Leu Val Pro
225                 230                 235                 240

Leu Glu Glu Pro Val Pro Ser His Trp Thr Met Val Pro Asp Glu Asp
                245                 250                 255

Phe Val Leu Ile Leu Ala Leu Leu His Ser His Leu Gly Ser Glu Met
            260                 265                 270

Phe Ala Ala Pro Met Gly Arg Cys Ala Ala Gly Val Met His Leu Phe
        275                 280                 285

Tyr Val Arg Ala Gly Val Ser Arg Ala Met Leu Leu Arg Phe Phe Leu
290                 295                 300
```

```
Ala Met Glu Lys Gly Arg His Met Glu Tyr Glu Cys Pro Tyr Leu Val
305                 310                 315                 320

Tyr Val Pro Val Val Ala Phe Arg Leu Glu Pro Lys Asp Gly Lys Gly
            325                 330                 335

Val Phe Ala Val Asp Gly Glu Leu Met Val Ser Glu Ala Val Gln Gly
            340                 345                 350

Gln Val His Pro Asn Tyr Phe Trp Met Val Ser Gly Cys Val Glu Pro
        355                 360                 365

Pro Ser Trp Lys Pro Gln Gln Met Pro Pro Glu Glu Pro Leu
        370                 375                 380

<210> SEQ ID NO 4
<211> LENGTH: 381
<212> TYPE: PRT
<213> ORGANISM: Mus musculus
<220> FEATURE:
<221> NAME/KEY: MISC_FEATURE
<222> LOCATION: (1)..(381)
<223> OTHER INFORMATION: SEQ ID NO 4 is the peptide sequence of mSPHK1a
      in Figure 3, corresponding to amino acid residue 124 to 504 of
      SPHK1a of GenBank sequence Accession Number AF068748. SEQ ID NO 4
      is equivalent to SEQ ID NO 1 that is the amino acid sequence of
      SPHK1a in Figure 1.
<300> PUBLICATION INFORMATION:
<301> AUTHORS: Kohama et al.,
<302> TITLE: Molecular cloning and functional characterization of murine
      sphingosine kinase
<303> JOURNAL: Journal of Biological Chemistry
<304> VOLUME: 273
<305> ISSUE: 37
<306> PAGES: 23722-23728
<307> DATE: 1998
<308> DATABASE ACCESSION NUMBER: AAC61697
<309> DATABASE ENTRY DATE: 1998-09-26
<313> RELEVANT RESIDUES: (124)..(504)
<300> PUBLICATION INFORMATION:
<308> DATABASE ACCESSION NUMBER: AAC61697
<309> DATABASE ENTRY DATE: 1998-09-26
<313> RELEVANT RESIDUES: (124)..(504)

<400> SEQUENCE: 4

Met Glu Pro Glu Cys Pro Arg Gly Leu Leu Pro Arg Pro Cys Arg Val
1               5                   10                  15

Leu Val Leu Leu Asn Pro Gln Gly Gly Lys Gly Lys Ala Leu Gln Leu
            20                  25                  30

Phe Gln Ser Arg Val Gln Pro Phe Leu Glu Glu Ala Glu Ile Thr Phe
        35                  40                  45

Lys Leu Ile Leu Thr Glu Arg Lys Asn His Ala Arg Glu Leu Val Cys
50                  55                  60

Ala Glu Glu Leu Gly His Trp Asp Ala Leu Ala Val Met Ser Gly Asp
65                  70                  75                  80

Gly Leu Met His Glu Val Val Asn Gly Leu Met Glu Arg Pro Asp Trp
                85                  90                  95

Glu Thr Ala Ile Gln Lys Pro Leu Cys Ser Leu Pro Gly Gly Ser Gly
            100                 105                 110

Asn Ala Leu Ala Ala Ser Val Asn His Tyr Ala Gly Tyr Glu Gln Val
        115                 120                 125

Thr Asn Glu Asp Leu Leu Ile Asn Cys Thr Leu Leu Leu Cys Arg Arg
    130                 135                 140

Arg Leu Ser Pro Met Asn Leu Leu Ser Leu His Thr Ala Ser Gly Leu
145                 150                 155                 160

Arg Leu Tyr Ser Val Leu Ser Leu Ser Trp Gly Phe Val Ala Asp Val
                165                 170                 175
```

-continued

```
Asp Leu Glu Ser Glu Lys Tyr Arg Arg Leu Gly Glu Ile Arg Phe Thr
            180                 185                 190

Val Gly Thr Phe Phe Arg Leu Ala Ser Leu Arg Ile Tyr Gln Gly Gln
            195                 200                 205

Leu Ala Tyr Leu Pro Val Gly Thr Val Ala Ser Lys Arg Pro Ala Ser
            210                 215                 220

Thr Leu Val Gln Lys Gly Pro Val Asp Thr His Leu Val Pro Leu Glu
225                 230                 235                 240

Glu Pro Val Pro Ser His Trp Thr Val Pro Glu Gln Asp Phe Leu
                245                 250                 255

Leu Val Leu Val Leu Leu His Thr His Leu Ser Ser Glu Leu Phe Ala
            260                 265                 270

Ala Pro Met Gly Arg Cys Glu Ala Gly Val Met His Leu Phe Tyr Val
            275                 280                 285

Arg Ala Gly Val Ser Arg Ala Ala Leu Leu Arg Leu Phe Leu Ala Met
            290                 295                 300

Gln Lys Gly Lys His Met Glu Leu Asp Cys Pro Tyr Leu Val His Val
305                 310                 315                 320

Pro Val Val Ala Phe Arg Leu Glu Pro Arg Ser Gln Arg Gly Val Phe
                325                 330                 335

Ser Val Asp Gly Glu Leu Met Val Cys Glu Ala Val Gln Gly Gln Val
            340                 345                 350

His Pro Asn Tyr Leu Trp Met Val Cys Gly Ser Arg Asp Ala Pro Ser
            355                 360                 365

Gly Arg Asp Ser Arg Arg Gly Pro Pro Glu Glu Pro
            370                 375                 380

<210> SEQ ID NO 5
<211> LENGTH: 373
<212> TYPE: PRT
<213> ORGANISM: Mus musculus
<220> FEATURE:
<221> NAME/KEY: MISC_FEATURE
<222> LOCATION: (1)..(373)
<223> OTHER INFORMATION: SEQ ID NO 5 is the peptide sequence of Mouse
      SPHK1a in Fig. 2, corresponding to amino acid residue 131 to 504
      of SPHK1a of GenBank sequence Accession Number AAC61697.
<300> PUBLICATION INFORMATION:
<308> DATABASE ACCESSION NUMBER: AAC61697
<309> DATABASE ENTRY DATE: 1998-09-26
<313> RELEVANT RESIDUES: (132)..(504)

<400> SEQUENCE: 5

Leu Leu Pro Arg Pro Cys Arg Val Leu Val Leu Leu Asn Pro Gln Gly
1               5                   10                  15

Gly Lys Gly Lys Ala Leu Gln Leu Phe Gln Ser Arg Val Gln Pro Phe
            20                  25                  30

Leu Glu Glu Ala Glu Ile Thr Phe Lys Leu Ile Leu Thr Glu Arg Lys
            35                  40                  45

Asn His Ala Arg Glu Leu Val Cys Ala Glu Glu Leu His Trp Asp
        50                  55                  60

Ala Leu Ala Val Met Ser Gly Asp Gly Leu Met His Glu Val Val Asn
65                  70                  75                  80

Gly Leu Met Glu Arg Pro Asp Trp Glu Thr Ala Ile Gln Lys Pro Leu
                85                  90                  95

Cys Ser Leu Pro Gly Gly Ser Gly Asn Ala Leu Ala Ala Ser Val Asn
            100                 105                 110
```

His Tyr Ala Gly Tyr Glu Gln Val Thr Asn Glu Asp Leu Leu Ile Asn
            115                 120                 125

Cys Thr Leu Leu Leu Cys Arg Arg Leu Ser Pro Met Asn Leu Leu
        130                 135                 140

Ser Leu His Thr Ala Ser Gly Leu Arg Leu Tyr Ser Val Leu Ser Leu
145                 150                 155                 160

Ser Trp Gly Phe Val Ala Asp Val Asp Leu Glu Ser Glu Lys Tyr Arg
                165                 170                 175

Arg Leu Gly Glu Ile Arg Phe Thr Val Gly Thr Phe Phe Arg Leu Ala
            180                 185                 190

Ser Leu Arg Ile Tyr Gln Gly Gln Leu Ala Tyr Leu Pro Val Gly Thr
        195                 200                 205

Val Ala Ser Lys Arg Pro Ala Ser Thr Leu Val Gln Lys Gly Pro Val
    210                 215                 220

Asp Thr His Leu Val Pro Leu Glu Glu Pro Val Pro Ser His Trp Thr
225                 230                 235                 240

Val Val Pro Glu Gln Asp Phe Leu Leu Val Leu Val Leu Leu His Thr
                245                 250                 255

His Leu Ser Ser Glu Leu Phe Ala Ala Pro Met Gly Arg Cys Glu Ala
            260                 265                 270

Gly Val Met His Leu Phe Tyr Val Arg Ala Gly Val Ser Arg Ala Ala
        275                 280                 285

Leu Leu Arg Leu Phe Leu Ala Met Gln Lys Gly Lys His Met Glu Leu
    290                 295                 300

Asp Cys Pro Tyr Leu Val His Val Pro Val Val Ala Phe Arg Leu Glu
305                 310                 315                 320

Pro Arg Ser Gln Arg Gly Val Phe Ser Val Asp Gly Glu Leu Met Val
                325                 330                 335

Cys Glu Ala Val Gln Gly Gln Val His Pro Asn Tyr Leu Trp Met Val
            340                 345                 350

Cys Gly Ser Arg Asp Ala Pro Ser Gly Arg Asp Ser Arg Arg Gly Pro
        355                 360                 365

Pro Pro Glu Glu Pro
    370

<210> SEQ ID NO 6
<211> LENGTH: 392
<212> TYPE: PRT
<213> ORGANISM: Caenorhabditis elegans
<220> FEATURE:
<221> NAME/KEY: MISC_FEATURE
<222> LOCATION: (1)..(392)
<223> OTHER INFORMATION: Corresponding to peptide seqence of c elegans
      in Figure 2.
<300> PUBLICATION INFORMATION:
<308> DATABASE ACCESSION NUMBER: T19707
<309> DATABASE ENTRY DATE: 1999-10-15
<313> RELEVANT RESIDUES: (82)..(473)

<400> SEQUENCE: 6

Glu Gln Cys Arg Gly Asn Leu Leu Val Phe Ile Asn Pro Asn Ser Gly
1               5                   10                  15

Thr Gly Lys Ser Leu Glu Thr Phe Ala Asn Thr Val Gly Pro Lys Leu
            20                  25                  30

Asp Lys Ser Leu Ile Arg Tyr Glu Val Val Thr Thr Gly Pro Asn
        35                  40                  45

His Ala Arg Asn Val Leu Met Thr Lys Ala Asp Leu Gly Lys Phe Asn
    50                  55                  60

Gly Val Leu Ile Leu Ser Gly Asp Gly Leu Val Phe Glu Ala Leu Asn
65                  70                  75                  80

Gly Ile Leu Cys Arg Glu Asp Ala Phe Arg Ile Phe Pro Thr Leu Pro
                85                  90                  95

Ile Gly Ile Val Pro Ser Gly Ser Gly Asn Gly Leu Leu Cys Ser Val
            100                 105                 110

Leu Ser Lys Tyr Gly Thr Lys Met Asn Glu Lys Ser Val Met Glu Arg
        115                 120                 125

Ala Leu Glu Ile Ala Thr Ser Pro Thr Ala Lys Ala Glu Ser Val Ala
    130                 135                 140

Leu Tyr Ser Val Lys Thr Asp Asn Gln Ser Tyr Ala Ser Phe Leu Ser
145                 150                 155                 160

Ile Gly Trp Gly Leu Met Ala Asp Ile Asp Ile Asp Ser Glu Lys Trp
                165                 170                 175

Arg Lys Ser Leu Gly His His Arg Phe Thr Val Met Gly Phe Ile Arg
            180                 185                 190

Ser Cys Asn Leu Arg Ser Tyr Lys Gly Arg Leu Thr Tyr Arg Pro Tyr
        195                 200                 205

Lys Pro Lys Gly Phe His Pro Ser Ser Asn Val Phe Ser Val Tyr Glu
    210                 215                 220

Lys Thr Thr Gln Gln Arg Ile Asp Asp Ser Lys Val Lys Thr Asn Gly
225                 230                 235                 240

Ser Val Ser Asp Ser Glu Glu Thr Met Glu Thr Lys Phe Gln Asn
                245                 250                 255

Trp Thr Leu Pro Asp Ser Asp Glu Thr Leu Ala Val Gly Ser Ser Asp
                260                 265                 270

Leu Glu Glu Thr Val Val Ile Glu Asp Asn Phe Val Asn Ile Tyr Ala
            275                 280                 285

Val Thr Leu Ser His Ile Ala Ala Asp Gly Pro Phe Ala Pro Ser Ala
    290                 295                 300

Lys Leu Glu Asp Asn Arg Ile His Leu Ser Tyr Ile Leu Trp Lys Asp
305                 310                 315                 320

Ile Gly Thr Arg Val Asn Ile Ala Lys Tyr Leu Leu Ala Ile Glu His
                325                 330                 335

Glu Thr His Leu Asp Leu Pro Phe Val Lys His Val Glu Val Ser Ser
            340                 345                 350

Met Lys Leu Glu Val Ile Ser Glu Gly Ser His Val Val Leu Asp Gly
        355                 360                 365

Glu Val Val Asp Thr Lys Thr Ile Glu Val Ala Ser Thr Lys Asn His
    370                 375                 380

Ile Ser Val Phe Ser Ser Thr Ala
385                 390

<210> SEQ ID NO 7
<211> LENGTH: 403
<212> TYPE: PRT
<213> ORGANISM: Saccharomyces cerevisiae
<220> FEATURE:
<221> NAME/KEY: MISC_FEATURE
<222> LOCATION: (1)..(403)
<223> OTHER INFORMATION: Corresponding to peptide sequence Yeast LCB4 in
      Figure 2.
<300> PUBLICATION INFORMATION:
<308> DATABASE ACCESSION NUMBER: NP 014814
<309> DATABASE ENTRY DATE: 2001-07-09
<313> RELEVANT RESIDUES: (222)..(624)

```
<400> SEQUENCE: 7

Asn Ser Lys Arg Asn Arg Ser Ile Leu Val Ile Ile Asn Pro His Gly
  1               5                  10                  15

Gly Lys Gly Thr Ala Lys Asn Leu Phe Leu Thr Lys Ala Arg Pro Ile
                 20                  25                  30

Leu Val Glu Ser Gly Cys Lys Ile Glu Ile Ala Tyr Thr Lys Tyr Ala
             35                  40                  45

Arg His Ala Ile Asp Ile Ala Lys Asp Leu Asp Ile Ser Lys Tyr Asp
         50                  55                  60

Thr Ile Ala Cys Ala Ser Gly Asp Gly Ile Pro Tyr Glu Val Ile Asn
 65                  70                  75                  80

Gly Leu Tyr Arg Arg Pro Asp Arg Val Asp Ala Phe Asn Lys Leu Ala
                 85                  90                  95

Val Thr Gln Leu Pro Cys Gly Ser Gly Asn Ala Met Ser Ile Ser Cys
            100                 105                 110

His Trp Thr Asn Asn Pro Ser Tyr Ala Ala Leu Cys Leu Val Lys Ser
            115                 120                 125

Ile Glu Thr Arg Ile Asp Leu Met Cys Cys Ser Gln Pro Ser Tyr Met
        130                 135                 140

Asn Glu Trp Pro Arg Leu Ser Phe Leu Ser Gln Thr Tyr Gly Val Ile
145                 150                 155                 160

Ala Glu Ser Asp Ile Asn Thr Glu Phe Ile Arg Trp Met Gly Pro Val
                165                 170                 175

Arg Phe Asn Leu Gly Val Ala Phe Asn Ile Ile Gln Gly Lys Lys Tyr
            180                 185                 190

Pro Cys Glu Val Phe Val Lys Tyr Ala Ala Lys Ser Lys Lys Glu Leu
        195                 200                 205

Lys Val His Phe Leu Glu Asn Lys Asp Lys Asn Lys Gly Cys Leu Thr
        210                 215                 220

Phe Glu Pro Asn Pro Ser Pro Asn Ser Ser Pro Asp Leu Leu Ser Lys
225                 230                 235                 240

Asn Asn Ile Asn Asn Ser Thr Lys Asp Glu Leu Ser Pro Asn Phe Leu
                245                 250                 255

Asn Glu Asp Asn Phe Lys Leu Lys Tyr Pro Met Thr Glu Pro Val Pro
            260                 265                 270

Arg Asp Trp Glu Lys Met Asp Ser Glu Leu Thr Asp Asn Leu Thr Ile
        275                 280                 285

Phe Tyr Thr Gly Lys Met Pro Tyr Ile Ala Lys Asp Thr Lys Phe Phe
290                 295                 300

Pro Ala Ala Leu Pro Ala Asp Gly Thr Ile Asp Leu Val Ile Thr Asp
305                 310                 315                 320

Ala Arg Ile Pro Val Thr Arg Met Thr Pro Ile Leu Leu Ser Leu Asp
                325                 330                 335

Lys Gly Ser His Val Leu Glu Pro Glu Val Ile His Ser Lys Ile Leu
            340                 345                 350

Ala Tyr Lys Ile Ile Pro Lys Val Glu Ser Gly Leu Phe Ser Val Asp
        355                 360                 365

Gly Glu Lys Phe Pro Leu Glu Pro Leu Gln Val Glu Ile Met Pro Met
    370                 375                 380

Leu Cys Lys Thr Leu Leu Arg Asn Gly Arg Tyr Ile Asp Thr Glu Phe
385                 390                 395                 400

Glu Ser Met
```

-continued

<210> SEQ ID NO 8
<211> LENGTH: 424
<212> TYPE: PRT
<213> ORGANISM: Saccharomyces cerevisiae
<220> FEATURE:
<221> NAME/KEY: MISC_FEATURE
<222> LOCATION: (1)..(424)
<223> OTHER INFORMATION: Corresponding to peptide sequence Yeast LCB5 in
      Figure 2.
<300> PUBLICATION INFORMATION:
<308> DATABASE ACCESSION NUMBER: NP 013361
<309> DATABASE ENTRY DATE: 2001-07-09
<313> RELEVANT RESIDUES: (264)..(687)

<400> SEQUENCE: 8

Asn Thr Arg Arg Asn Lys Ser Ile Phe Val Ile Ile Asn Pro Phe Gly
1               5                   10                  15

Gly Lys Gly Lys Ala Lys Lys Leu Phe Met Thr Lys Ala Lys Pro Leu
            20                  25                  30

Leu Leu Ala Ser Arg Cys Ser Ile Glu Val Val Tyr Thr Lys Tyr Pro
        35                  40                  45

Gly His Ala Ile Glu Ile Ala Arg Glu Met Asp Ile Asp Lys Tyr Asp
    50                  55                  60

Thr Ile Ala Cys Ala Ser Gly Asp Gly Ile Pro His Glu Val Ile Asn
65                  70                  75                  80

Gly Leu Tyr Gln Arg Pro Asp His Val Lys Ala Phe Asn Asn Ile Ala
                85                  90                  95

Ile Thr Glu Ile Pro Cys Gly Ser Gly Asn Ala Met Ser Val Ser Cys
            100                 105                 110

His Trp Thr Asn Asn Pro Ser Tyr Ser Thr Leu Cys Leu Ile Lys Ser
        115                 120                 125

Ile Glu Thr Arg Ile Asp Leu Met Cys Cys Ser Gln Pro Ser Tyr Ala
    130                 135                 140

Arg Glu His Pro Lys Leu Ser Phe Leu Ser Gln Thr Tyr Gly Leu Ile
145                 150                 155                 160

Ala Glu Thr Asp Ile Asn Thr Glu Phe Ile Arg Trp Met Gly Pro Ala
                165                 170                 175

Arg Phe Glu Leu Gly Val Ala Phe Asn Ile Ile Gln Lys Lys Lys Tyr
            180                 185                 190

Pro Cys Glu Ile Tyr Val Lys Tyr Ala Ala Lys Ser Lys Asn Glu Leu
        195                 200                 205

Lys Asn His Tyr Leu Glu His Lys Asn Lys Gly Ser Leu Glu Phe Gln
    210                 215                 220

His Ile Thr Met Asn Lys Asp Asn Glu Asp Cys Asp Asn Tyr Asn Tyr
225                 230                 235                 240

Glu Asn Glu Tyr Glu Thr Glu Asn Glu Asp Glu Asp Ala Asp
                245                 250                 255

Ala Asp Asp Glu Asp Ser His Leu Ile Ser Arg Asp Leu Ala Asp Ser
            260                 265                 270

Ser Ala Asp Gln Ile Lys Glu Glu Asp Phe Lys Ile Lys Tyr Pro Leu
        275                 280                 285

Asp Glu Gly Ile Pro Ser Asp Trp Glu Arg Leu Asp Pro Asn Ile Ser
    290                 295                 300

Asn Asn Leu Gly Ile Phe Tyr Thr Gly Lys Met Pro Tyr Val Ala Ala
305                 310                 315                 320

Asp Thr Lys Phe Phe Pro Ala Ala Leu Pro Ser Asp Gly Thr Met Asp
                325                 330                 335

```
Met Val Ile Thr Asp Ala Arg Thr Ser Leu Thr Arg Met Ala Pro Ile
            340                 345                 350

Leu Leu Gly Leu Asp Lys Gly Ser His Val Leu Gln Pro Glu Val Leu
            355                 360                 365

His Ser Lys Ile Leu Ala Tyr Lys Ile Ile Pro Lys Leu Gly Asn Gly
    370                 375                 380

Leu Phe Ser Val Asp Gly Glu Lys Phe Pro Leu Glu Pro Leu Gln Val
385                 390                 395                 400

Glu Ile Met Pro Arg Leu Cys Lys Thr Leu Leu Arg Asn Gly Arg Tyr
                405                 410                 415

Val Asp Thr Asp Phe Asp Ser Met
            420
```

<210> SEQ ID NO 9
<211> LENGTH: 204
<212> TYPE: PRT
<213> ORGANISM: Unknown
<220> FEATURE:
<223> OTHER INFORMATION: Putative kinase sequence obtained by assembling
      sequences from several human ESTs (accession numbers D31133,
      AA232791, W63556, AA081152 and AA026479).
<221> NAME/KEY: MISC_FEATURE
<222> LOCATION: (1)..(204)
<223> OTHER INFORMATION: Corresponding to peptide sequence Putative
      Human in Figure 2.

<400> SEQUENCE: 9

```
Leu Asn Pro Arg Gly Gly Lys Gly Lys Ala Leu Gln Leu Phe Arg Ser
1               5                   10                  15

His Val Gln Pro Leu Leu Ala Glu Ala Glu Ile Ser Phe Thr Leu Met
                20                  25                  30

Leu Thr Glu Arg Arg Asn His Ala Arg Glu Leu Val Arg Ser Glu Glu
            35                  40                  45

Leu Gly Arg Trp Asp Ala Leu Val Val Met Ser Gly Asp Gly Leu Met
    50                  55                  60

His Glu Val Val Asn Gly Leu Met Glu Arg Pro Asp Trp Glu Thr Ala
65                  70                  75                  80

Ile Gln Lys Pro Leu Cys Ser Leu Pro Ala Gly Ser Gly Asn Ala Leu
                85                  90                  95

Ala Ala Ser Leu Asn His Tyr Ala Gly Tyr Glu Leu Phe Ser Val Leu
            100                 105                 110

Ser Leu Ala Trp Gly Phe Ile Ala Asp Val Asp Leu Glu Ser Glu Lys
    115                 120                 125

Tyr Arg Arg Leu Gly Glu Met Arg Phe Thr Leu Gly Thr Phe Leu Arg
130                 135                 140

Leu Ala Ala Leu Arg Thr Tyr Arg Gly Arg Leu Ala Thr Leu Pro Val
145                 150                 155                 160

Gly Arg Val Gly Ser Lys Val Val Ala Phe Arg Leu Glu Pro Arg Asn
                165                 170                 175

Gly Lys Gly Val Phe Ala Val Asp Gly Glu Leu Met Val Ser Glu Ala
            180                 185                 190

Val Gln Gly Gln Leu His Pro Asn Tyr Leu Trp Met
    195                 200
```

<210> SEQ ID NO 10
<211> LENGTH: 240
<212> TYPE: PRT
<213> ORGANISM: UNKNOWN

-continued

<220> FEATURE:
<223> OTHER INFORMATION: SEQ ID NO 10 is the consensus sequence derived
      from mouse SPHK1A, C elegans, Yeast LCB4, Yeast LCB5 and putative
      human sphingosine kinase.
<221> NAME/KEY: MISC_FEATURE
<222> LOCATION: (1)..(240)
<223> OTHER INFORMATION: Corresponding to peptide sequence Consensus in
      Figure 10.
<221> NAME/KEY: X
<222> LOCATION: (1)..(240)
<223> OTHER INFORMATION: X cannotes any amino acid residue or a blank
      space.

<400> SEQUENCE: 10

Xaa Xaa Xaa Arg Xaa Xaa Xaa Xaa Val Xaa Ile Asn Pro Xaa Gly
1               5                   10                  15

Gly Lys Gly Lys Ala Xaa Xaa Leu Phe Xaa Xaa Xaa Xaa Pro Xaa
            20                  25                  30

Leu Xaa Xaa Xaa Xaa Xaa Xaa Xaa Xaa Xaa Thr Xaa Xaa Xaa
        35                  40                  45

Xaa His Ala Xaa Xaa Xaa Xaa Xaa Xaa Asp Xaa Xaa Xaa Xaa
    50                  55                  60

Asp Xaa Leu Ala Xaa Xaa Ser Gly Asp Gly Leu Xaa Xaa Glu Val Ile
65                  70                  75                  80

Asn Gly Leu Xaa Xaa Arg Xaa Asp Xaa Xaa Ala Xaa Xaa Xaa Xaa
                85                  90                  95

Xaa Xaa Xaa Xaa Xaa Pro Xaa Gly Ser Gly Asn Ala Xaa Xaa Xaa Ser
            100                 105                 110

Xaa Xaa Xaa Xaa Xaa Xaa Xaa Xaa Ser Xaa Leu Ser Xaa Xaa
        115                 120                 125

Xaa Gly Xaa Xaa Ala Xaa Xaa Asp Ile Xaa Ser Glu Xaa Xaa Arg Xaa
    130                 135                 140

Xaa Xaa Gly Xaa Xaa Arg Phe Xaa Xaa Gly Xaa Phe Xaa Xaa Xaa Xaa
145                 150                 155                 160

Xaa Xaa Arg Xaa Xaa Xaa Xaa Xaa Xaa Xaa Xaa Xaa Xaa Xaa
        165                 170                 175

Xaa Xaa Xaa Xaa Xaa Xaa Xaa Xaa Xaa Xaa Xaa Xaa Xaa Xaa
            180                 185                 190

Xaa Xaa Phe Xaa Val Asp Gly Glu Xaa Xaa Xaa Xaa Xaa Xaa Xaa
    195                 200                 205

Xaa Xaa Xaa Xaa Xaa Xaa Xaa Xaa Xaa Xaa Xaa Xaa Xaa Xaa Xaa
210                 215                 220

Xaa Xaa Xaa Xaa Xaa Xaa Xaa Xaa Xaa Xaa Xaa Xaa Xaa Xaa Xaa
225                 230                 235                 240

<210> SEQ ID NO 11
<211> LENGTH: 27
<212> TYPE: PRT
<213> ORGANISM: Unknown
<220> FEATURE:
<223> OTHER INFORMATION: Calcium/calmodulin binding consensus sequence
      of type B motif.
<221> NAME/KEY: MISC_FEATURE
<222> LOCATION: (1)..(27)
<223> OTHER INFORMATION: Corresponding to type B motif shown in line 32,
      page 6.
<221> NAME/KEY: X
<222> LOCATION: (1)..(27)
<223> OTHER INFORMATION: X connotes to any amino acid residue.

```
<400> SEQUENCE: 11

Phe Ile Leu Val Trp Xaa Xaa Xaa Xaa Xaa Xaa Phe Ala Ile Leu Val
1               5                   10                  15

Trp Xaa Xaa Xaa Xaa Xaa Phe Ile Leu Val Trp
            20                  25

<210> SEQ ID NO 12
<211> LENGTH: 32
<212> TYPE: PRT
<213> ORGANISM: Unknown
<220> FEATURE:
<223> OTHER INFORMATION: Calcium/calmodulin binding concensus sequence
      of type A motif.
<221> NAME/KEY: MISC_FEATURE
<222> LOCATION: (1)..(32)
<223> OTHER INFORMATION: Corresponding to Type A motif in line 1, page
      7.
<221> NAME/KEY: X
<222> LOCATION: (1)..(32)
<223> OTHER INFORMATION: X connotes any amino acid residue.

<400> SEQUENCE: 12

Phe Ile Leu Val Trp Xaa Xaa Xaa Phe Ala Ile Leu Val Trp Xaa Xaa
1               5                   10                  15

Phe Ala Ile Leu Val Trp Xaa Xaa Xaa Xaa Xaa Phe Ile Leu Val Trp
            20                  25                  30

<210> SEQ ID NO 13
<211> LENGTH: 16
<212> TYPE: DNA
<213> ORGANISM: Unknown
<220> FEATURE:
<223> OTHER INFORMATION: Artificial sequence of the gene-specific
      antisense primer hspk1-ASP1, shown in line 25, page 7.
<221> NAME/KEY: misc_feature
<222> LOCATION: (1)..(16)
<223> OTHER INFORMATION: Corresponding to sequence of the gene-specific
      antisense primer hspk1-ASP1, shown in line 25, page 7.

<400> SEQUENCE: 13
accattgtcc agtgag                                                    16

<210> SEQ ID NO 14
<211> LENGTH: 20
<212> TYPE: DNA
<213> ORGANISM: Unknown
<220> FEATURE:
<223> OTHER INFORMATION: Artifical sequence of  antisense primer
      hspk1-GSP2, shown in line 29-30, page 7.
<221> NAME/KEY: misc_feature
<222> LOCATION: (1)..(20)
<223> OTHER INFORMATION: Corresponding to the sequence of antisense
      primer hspk1-GSP2 in line 29-30, page 7.

<400> SEQUENCE: 14
ttcctacagg gaggtaggcc                                                20

<210> SEQ ID NO 15
<211> LENGTH: 20
<212> TYPE: DNA
<213> ORGANISM: Unknown
<220> FEATURE:
<223> OTHER INFORMATION: Artifical sequence of antisenese primer
      hspk1-GSP, shown in line 34, page 7.
<221> NAME/KEY: misc_feature
<222> LOCATION: (1)..(20)
<223> OTHER INFORMATION: Corresponding to the sequence of antisense
      primer hspk1-GSP3, shown in line 34, page 7.
```

-continued

```
<400> SEQUENCE: 15
ggctgccaga cgcaggaagg                                                    20

<210> SEQ ID NO 16
<211> LENGTH: 27
<212> TYPE: DNA
<213> ORGANISM: Unknown
<220> FEATURE:
<223> OTHER INFORMATION: Artifical sequence of sense primer sphk1-GSP4,
      shown in line 4-5, page 8.
<221> NAME/KEY: misc_feature
<222> LOCATION: (1)..(27)
<223> OTHER INFORMATION: Corresponding to artifical sequence of the
      sense primer sphk1-SGP4 in line 4-5, page 8.

<400> SEQUENCE: 16
gccaccatgg atccagcggg cggcccc                                            27

<210> SEQ ID NO 17
<211> LENGTH: 30
<212> TYPE: DNA
<213> ORGANISM: Unknown
<220> FEATURE:
<223> OTHER INFORMATION: Artifical sequence of the antisense primer
      sphk1-GSP5 in line 5-6, page 8.
<221> NAME/KEY: misc_feature
<222> LOCATION: (1)..(30)
<223> OTHER INFORMATION: Corresponding to the artifical sequence of
      antisense primer sphk1-GSP5 in line 5-6, page 8.

<400> SEQUENCE: 17
tcataagggc tcttctggcg gtggcatctg                                         30
```

What I claim is:

1. An isolated and substantially purified DNA molecule encoding mammalian sphingosine kinase, wherein said DNA molecule encodes a peptide sequence as specified in SEQ ID NO: 3.

2. A host cell transfected with DNA encoding mammalian sphingosine kinase, wherein said DNA encodes a peptide sequence as specified in SEQ ID NO: 3.

3. A recombinant DNA construct comprising:
   i) a vector and
   ii) DNA encoding a mammalian spningosine kinase, wherein said DNA encodes a peptide sequence as specified in SEQ ID NO: 3.

4. An isolated and substantially purified DNA molecule encoding the polypeptide sequence of SEQ ID NO: 3.

* * * * *